United States Patent
Harris et al.

(10) Patent No.: US 6,756,206 B2
(45) Date of Patent: Jun. 29, 2004

(54) ADSORPTION AND REMOVAL OF ENDOTOXIN FROM PHYSIOLOGICAL FLUIDS USING CATIONIC HELIX PEPTIDES

(75) Inventors: Robert B. Harris, Midlothian, VA (US); Russell L. Wolz, Richmond, VA (US); Gabriella Wolz, Richmond, VA (US)

(73) Assignee: Commonwealth Biotechnologies, Inc., Richmond, VA (US)

( * ) Notice: Subject to any disclaimer, the term of this patent is extended or adjusted under 35 U.S.C. 154(b) by 428 days.

(21) Appl. No.: 09/905,691

(22) Filed: Feb. 14, 2001

(65) Prior Publication Data

US 2002/0164329 A1 Nov. 7, 2002

Related U.S. Application Data

(63) Continuation-in-part of application No. 09/166,930, filed on Oct. 6, 1998, now Pat. No. 6,200,955.

(51) Int. Cl.$^7$ .................. G01N 33/68; A61K 38/10; A61K 38/16; C07K 7/08
(52) U.S. Cl. .................. 435/7.1; 514/13; 530/326
(58) Field of Search ............... 435/7.1; 514/13; 530/326

(56) References Cited

U.S. PATENT DOCUMENTS

| | | | | |
|---|---|---|---|---|
| H001509 | H | * 12/1995 | Eran et al. | 530/383 |
| 5,506,204 | A | * 4/1996 | Aston | 514/8 |
| 5,877,153 | A | * 3/1999 | Harris et al. | 514/13 |

* cited by examiner

*Primary Examiner*—Robert A. Wax
(74) *Attorney, Agent, or Firm*—Burns Doane Swecker & Mathis, LLP (57) ABSTRACT

The present invention provides endotoxin-binding peptides which are useful in the treatment and prevention of sepsis. The present invention further provides a method for treating or preventing sepsis comprising administration of the compounds of the present invention.

9 Claims, 7 Drawing Sheets

SEQUENCE LISTING

```
<160> NUMBER OF SEQ ID NOS: 5

<210> SEQ ID NO 1
<211> LENGTH: 16
<212> TYPE: PRT
<213> ORGANISM: Artificial Sequence
<220> FEATURE:
<223> OTHER INFORMATION: Arginine Helix #3

<400> SEQUENCE: 1

Ala Glu Ala Arg Ala Arg Arg Ala Ala Ala Arg Ala Ala Arg Arg Ala
 1               5                  10                  15

<210> SEQ ID NO 2
<211> LENGTH: 19
<212> TYPE: PRT
<213> ORGANISM: Artificial Sequence
<220> FEATURE:
<223> OTHER INFORMATION: Bis-Arginine Helix #2

<400> SEQUENCE: 2

Ala Arg Ala Ala Arg Arg Ala Ala Arg Ala Ala Ala Arg Arg Ala Arg
 1               5                  10                  15

Ala Glu Ala

<210> SEQ ID NO 3
<211> LENGTH: 19
<212> TYPE: PRT
<213> ORGANISM: Artificial Sequence
<220> FEATURE:
<223> OTHER INFORMATION: Arginine Helix #2

<400> SEQUENCE: 3

Ala Glu Ala Arg Ala Arg Arg Ala Ala Ala Arg Ala Ala Arg Arg Ala
 1               5                  10                  15

Ala Arg Ala

<210> SEQ ID NO 4
<211> LENGTH: 16
<212> TYPE: PRT
<213> ORGANISM: Artificial Sequence
<220> FEATURE:
<223> OTHER INFORMATION: Tris-Arginine Helix #3

<400> SEQUENCE: 4

Ala Arg Arg Ala Ala Arg Ala Ala Ala Arg Arg Ala Arg Ala Glu Ala
 1               5                  10                  15

<210> SEQ ID NO 5
<211> LENGTH: 16
<212> TYPE: PRT
<213> ORGANISM: Artificial Sequence
<220> FEATURE:
<223> OTHER INFORMATION: Tris-Arginine Helix #3
```

-continued

```
<400> SEQUENCE: 5

Cys Arg Arg Ala Ala Arg Ala Ala Arg Arg Ala Arg Ala Glu Ala
1               5                   10                  15
```

ADSORPTION AND REMOVAL OF ENDOTOXIN FROM PHYSIOLOGICAL FLUIDS USING CATIONIC HELIX PEPTIDES

CROSS REFERENCE TO RELATED APPLICATIONS

This application is a continuation-in-part of U.S. patent application Ser. No. 09/166,930 filed Oct. 6, 1998, (now U.S. Pat. No. 6,200,955), the contents of which are incorporated herein by reference.

BACKGROUND OF THE INVENTION

1. Field of the Invention

The present invention provides endotoxin-binding peptides which are useful in the treatment and prevention of sepsis. The present invention further provides a method for treating or preventing sepsis comprising administration of the compounds of the present invention.

2. Description of the Related Art

The incidence of sepsis in the United States is approximately 500,000 cases per year, of which the mortality incidence ranges from 35 to 65% (Dellinger, Opal et al. 1997). Despite the most modern of intensive life support measures, this means that 100,000 to 300,000 people die each year in the United States from endotoxic shock (sepsis). It is estimated that the annual cost in treating these patients is 5 to 10 billion dollars (Dellinger, Opal et al. 1997). Severe sepsis is initiated by an acute infection which leads to local and systemic release of bacterial products.

There are numerous, well characterized bacterial and host mediators of inflammation, all of which likely make a significant contribution in cases of overwhelming infection. It is also well known that the host inflammatory response leads to tissue injury, shock, and multiple organ dysfunction and in the majority of cases, release of bacterial endotoxins is the primary causative agent of endotoxic shock.

Endotoxin, or lipopolysaccharides (LPS) of gram-negative bacteria, are potent stimulators of the production and release of cytokines and pro-inflammatory mediators. Endotoxin causes activation of macrophages and induces the production of monokines, particularly tissue necrosis factor (TNF- and TNF-) and interleukin −1 (IL-1) (Parrillo 1993; Tracey and Cerami 1993). Other mediators of inflammation include IL-6, IL-8, nitric oxide (NO) platelet activating factor, prostaglandin, leukotrienes, complement components, and kinins (Tracey and Cerami 1993). The cumulative effect of all these mediators is disseminated intravascular coagulation, multiple organ failure and most often, death.

Thus, development of an anti-LPS agent seems a rational approach to treatment of gram negative bacterial infection. However, whereas anti-TNF antibody treatment has proved somewhat effective in some selected clinical trials (Tracey and Cerami 1993; Tracey 1994), to date, targeting endotoxin with monoclonal antibodies as a method of treatment has proved ineffective. This may be because the antibodies lack in vivo neutralizing activity or because endotoxin is not the appropriate target for intervention. Or it may be because the antibodies do not possess sufficient cross-strain reactivities or because the antibodies do not bind LPS while it is still resident in the bacterial membrane. Regardless, there is a pressing demand for a clinically useful, safe therapy for removal of endotoxin from the bloodstream.

Different classes of anti-LPS agents are currently in development. Lipid A derivatives (such as E5331) may block or reverse endotoxin induced effects. Other agents, such as monophosphorylated Lipid A are meant to produce tolerance to endotoxin mediated effects and may have partial prophylactic utility. Still other agents in development include peptides, proteins, or lipoproteins which bind, neutralize and facilitate clearance of endotoxin. One such protein is recombinant heparin binding protein (rHBP; formerly known as cationic antimicrobial protein or bactericidal/permeability increasing factor) (Heinzelmann, Mercer-Jones et al. 2000). rHBP was administered to mice at different concentrations and at different intervals before and after cecal ligation and puncture. Survival was increased in mice pretreated well in advance with rHBP and was increased significantly, compared to controls, in animals treated with cefoxitin (an antibiotic) and rHBP. However, in animals treated with rHBP at the time of ligation and puncture, survival was not significantly different than that in the control group. Other proteins that have been tested include recombinant antithrombin III and LPS binding protein.

The interaction of LPS with its cognate binding protein has not yet been structurally elucidated. However, Ferguson et al (Ferguson, Welte et al. 2000) recently modeled the binding between LPS with the integral outer membrane protein FhuA from *Escherichia coli*. In accord with the results of previous mass spec and NMR studies, the model showed that the preponderance of stabilizing binding interactions occurred between 8 positively charged residues of FhuA (provided by Lys residue) and negatively charged functional groups resident on LPS. The three dimensional motif of FhuA was used to search the existing protein data base and a subset of 4 individual residues was found to be conserved in different proteins recognized to bind LPS. This subset of 4 residues was thus postulated to provide the structural pattern of recognition for binding LPS. Interestingly, LPS binding protein which binds circulating LPS or LPS embedded in whole bacteria also retains this conserved motif. Transfer of LPS from LPS binding protein to soluble or membrane bound CD14 receptor is thought to trigger the LPS signaling cascade which in turn, sets off the systemic inflammatory response. Ferguson et al. suggested that the conserved motif could serve as a template for molecular modeling of an LPS scavenger model which would be designed to reduced septic shock.

In the absence of an effective anti-LPS agent, other treatment paradigms are being tested. For instance, continuous venovenous hemofiltration has been used effectively in canine or porcine models of septic shock and in human intervention to remove inflammatory mediators from the circulation (Hoffinann, Hartl et al. 1996; Murphy, Fessler et al. 1997). Here, the blood flow is directed through a high flow ultrafiltration device which allows the relatively low molecular weight inflammatory mediators to be removed. The blood is then redirected into the patient. In the animal models, infusion of LPS causes severe hypodynamic circulatory state with significant depression of mean arterial pressure and cardiac output with a concomitant increase in pulmonary artery pressure. By and large, however, continuous ultrafiltration caused an improvement in global hemodynamics, increased hepatic blood flow, decreased blood lactate and nitrite/nitrate concentrations while also eliminating several anaphylatoxins from the circulation. High flow ultrafiltration is still under consideration as a treatment for sepsis.

SUMMARY OF THE INVENTION

Previously a family of multi-chain helix peptides have been developed which contain up to 4 copies of single helix sequences (see U.S. Pat. No. 5,877,133, the contents of which is incorporated herein by reference). These peptides present a conformer of high cationic charge density. The present inventors have unexpectedly discovered that three of these helix family members, namely Tris Arg Helix #3, Tetra Arg Helix #3 and Tris Arg Helix #3 (constrained) possess potent endotoxin binding activity. In an in vitro assay format, as little as 1 mg/ml of any one of these peptides quantitatively binds upwards of 1 µg/mL endotoxin in either water or plasma solution. The consequence of binding is that endotoxin is quantitatively sequestered from the plasma or aqueous solution. The key points of the present invention are thus:

1. The specified helix family peptides can be used to bind endotoxin in an in vitro assay format and can thus be used as part of a diagnostic for the presence of endotoxin in physiological fluids, including plasma, saliva, urine, or feces or in tissue samples.
2. The specified helix family peptides can be used to bind endotoxin in vivo and thus can be used as a singular or conjunctive therapy for removing endotoxin from the circulation.
3. The specified helix family peptides can be immobilized on surfaces to act as an affinity trap for endotoxin in ultrafiltration or dialysis-type treatments.
4. The specified helix family peptides can be used to bind and remove endotoxin from plasma fractionation products and virtually all other pharmaceutical preparations intended for human or veterinary use.
5. The specified helix family peptides can be used as a diagnostic tool to detect endotoxin in plasma fractionation products and virtually all other pharmaceutical preparations intended for human or veterinary use.
6. The specified helix family peptides serve as a model framework for endotoxin binding upon which new analogs are being designed through a process of molecular dynamics and binding simulations.

BRIEF DESCRIPTION OF THE DRAWINGS

FIG. 1. Structures of Bis-Arg Helix #2 (SEQ ID NOS.:2 and 3) (FIG. 1A), Tris-Arg Helix #3 (SEQ ID NO.:4)(FIG. 1B), and Tetra-Arg Helix #3 (SEQ ID NO:4) (FIG. 1C).

DETAILED DESCRIPTION OF THE PREFERRED EMBODIMENTS OF THE INVENTION

Compounds and Compositions

Figure 1A:
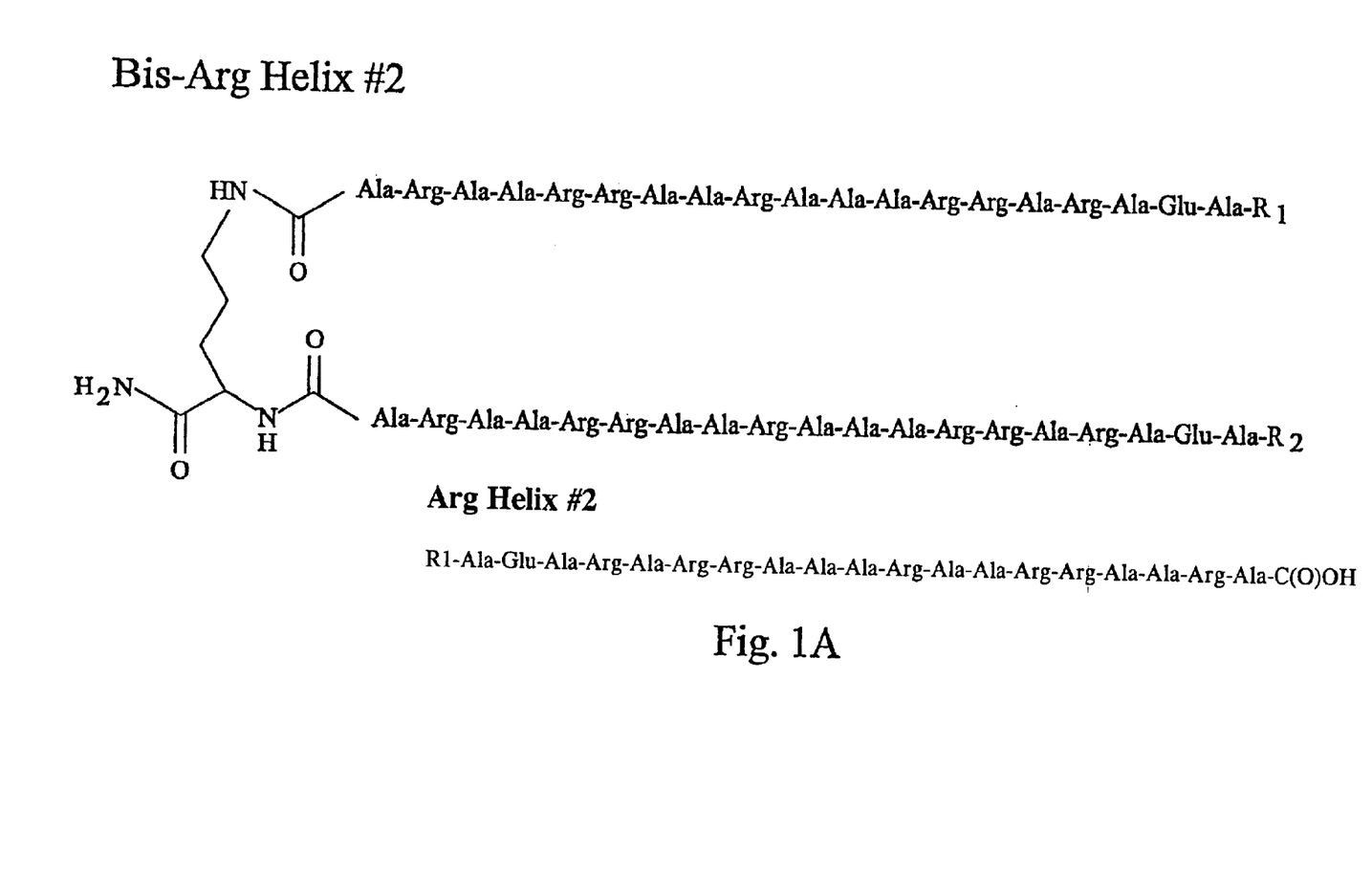
Figure 1B:
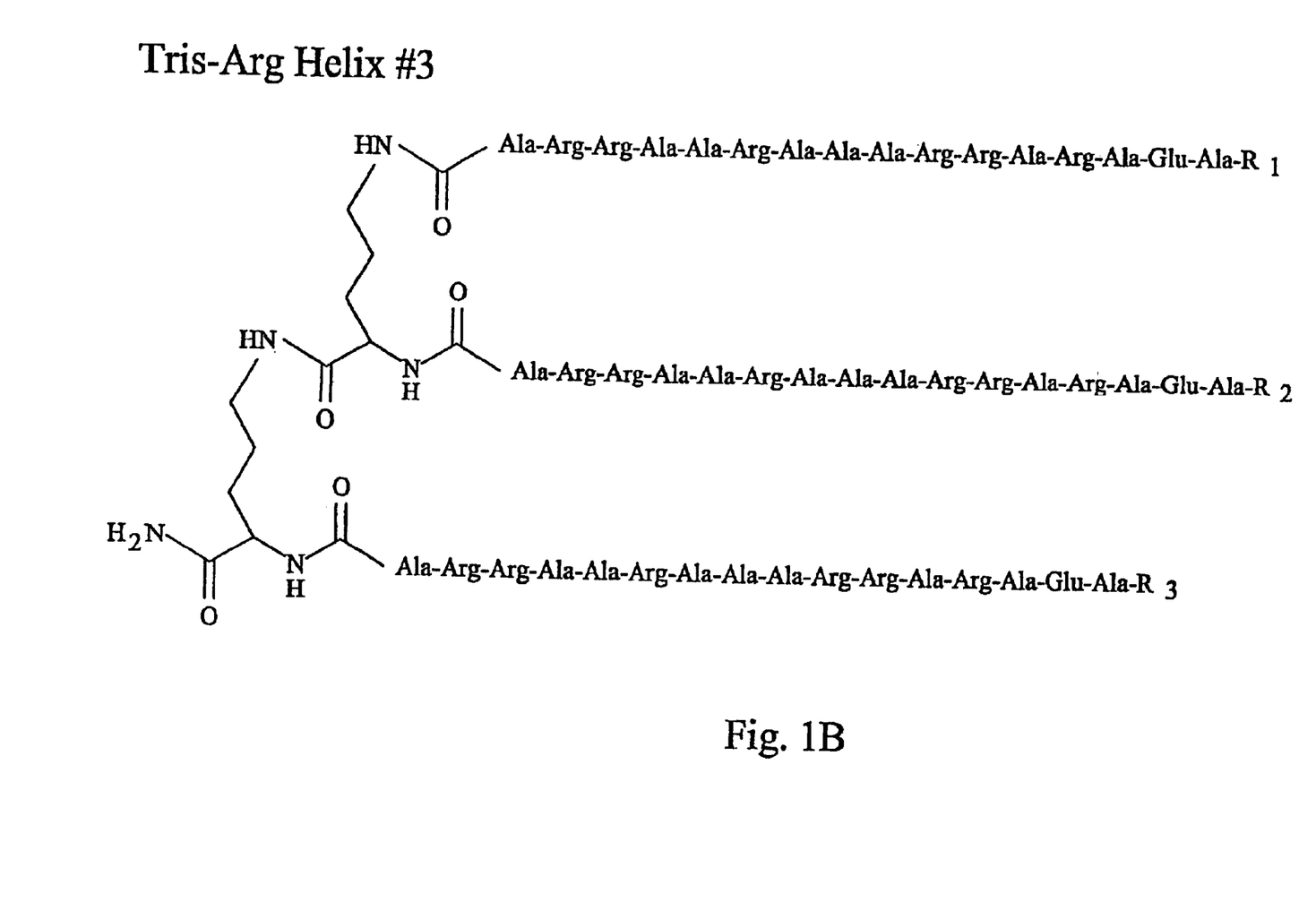
Figure 1C:
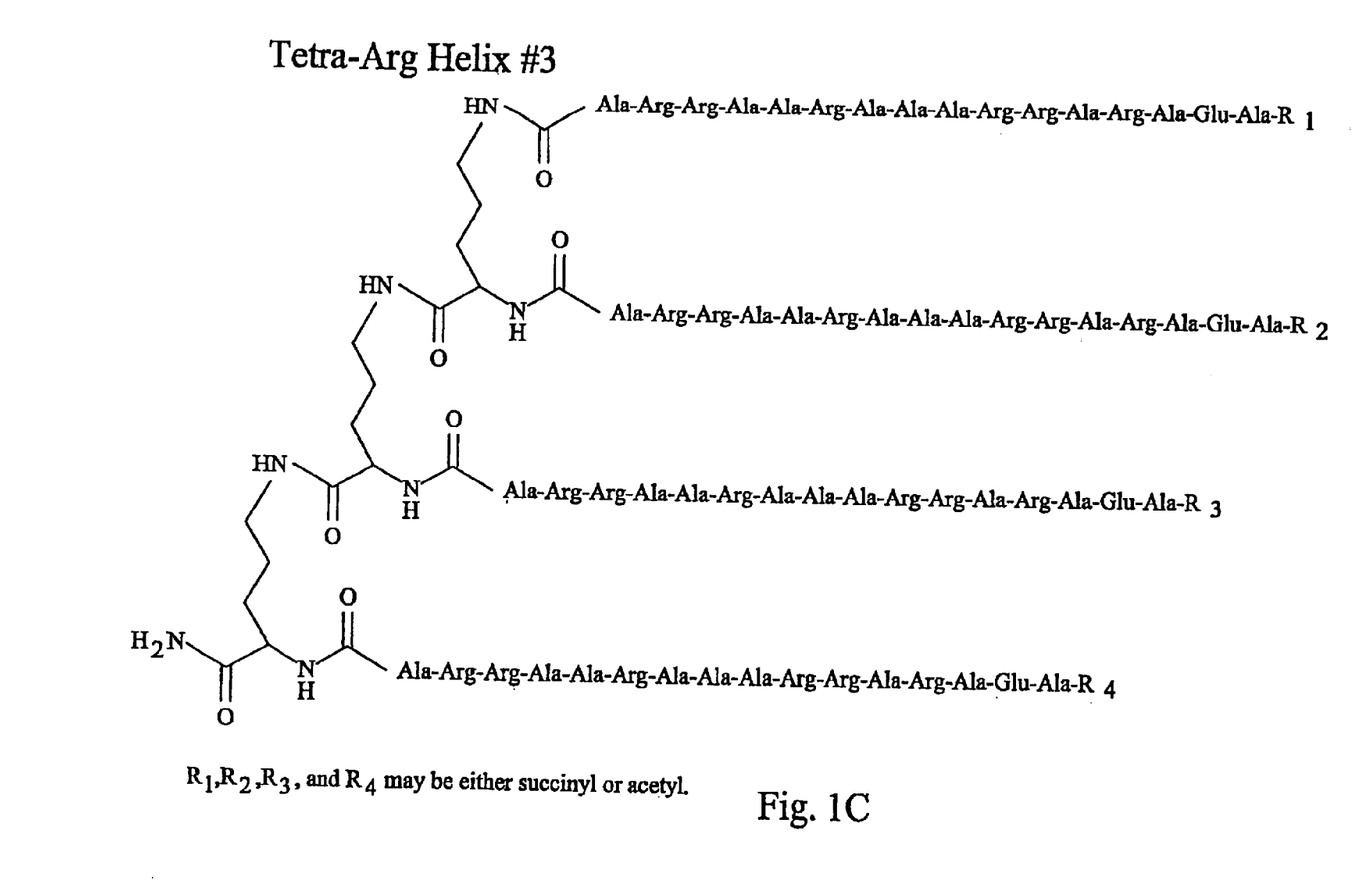

The peptides for use in the present invention are preferably branched-chain peptides such as Tris-ARG HELIX #3 and Tetra-ARG HELIX #3. The structures of these branched-chain peptides are displayed in FIG. 1.

Figure 2:
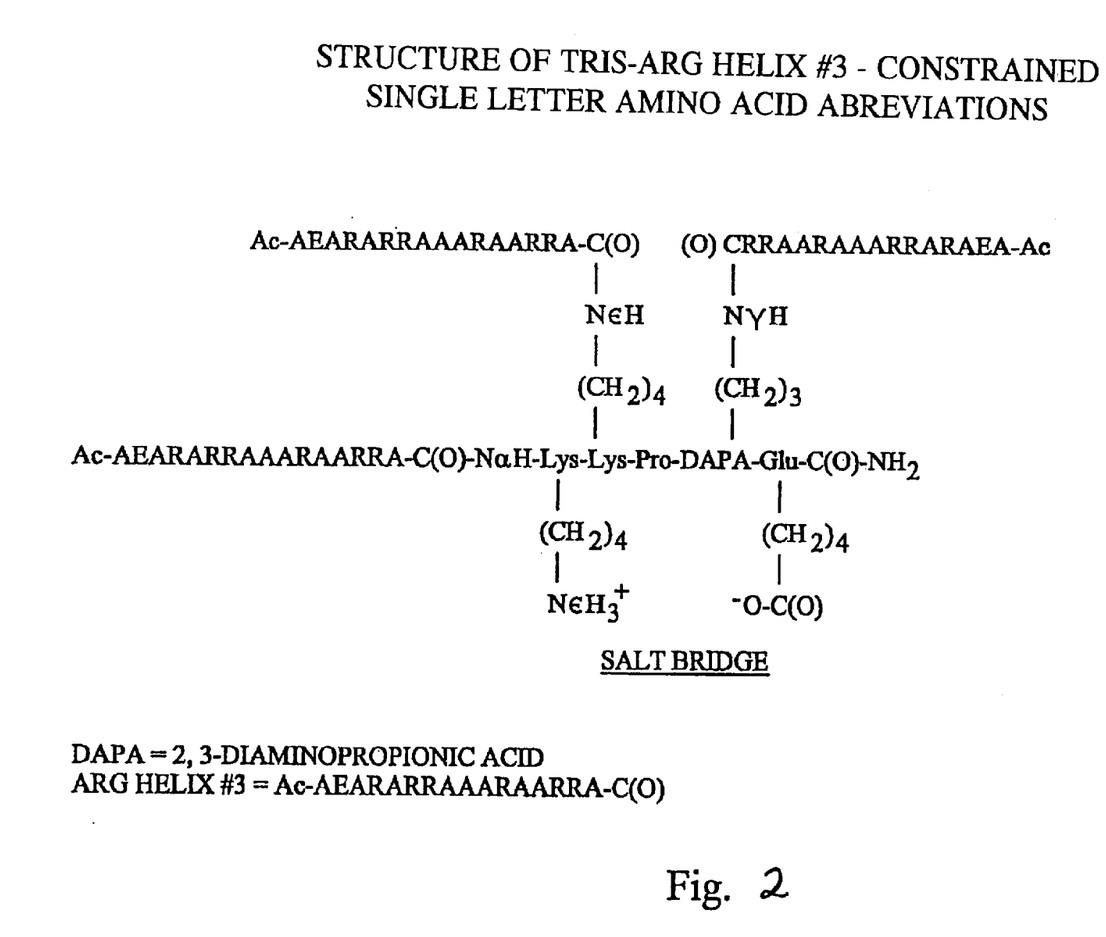
FIG. 2. Structure of Tris Arg #3 Constrained ("TR3 CONST") (SEQ ID NOS: 1 and 5.

An alternative preferred compound according to the present invention is Tris ARG #3 Constrained (hereafter "TR3 CONST"). TR3 CONST is simpler to synthesize in large scale, and hence is likely to be more amenable to commercialization. TR3 CONST is a "constrained" analog of Tris-ARG HELIX #3; it was designed with the use of molecular modeling and computational dynamics to place the three helix arms into a constrained, or restricted, conformation. The sequence of TR3 CONST at the critical "tether" or backbone region is different from Tris-ARG HELIX #3, but the binding arms are identical (see FIG. 2). Thus, the sequence of TR3 CONST is:

$$\text{ArgHel\#3—NH—Lys-Lys-Pro-DAPA-Glu—C(O)—NH}_2$$
$$\begin{array}{ccc} | & | & | \\ {}^+\text{H}_3\text{N} & \text{NH} & \text{NH} \\ | & | \\ \text{ArgHel\#}_3 & \text{ArgHel\#}_3 \end{array}$$

Arg Helix #3 (SEQ ID NO.1): N(acetyl)-AEARARRAAARAARRA-C(O)

As used herein, the peptides contemplated by the present invention include derivatives of those known in the art, in particular, the above-identified peptides, having any substitutions which do not eliminate or significantly reduce their ability to bind to endotoxins. For example, the peptides of the present invention are optionally substituted with a functional group. Any art-recognized functional group which does not eliminate or significantly reduce the peptides' ability to bind to endotoxins are contemplated, including, but not limited to, ester, amide, acid, amine, alcohol, ether, thioether, etc. Solvates, e.g., hydrates of the peptides useful in the methods of the present invention, are also included within the scope of the present invention. Methods of solvation to produce such solvates are generally known in the art.

Pharmaceutical salts of the endotoxin-binding peptides suitable for administration by a variety of routes are known in the art and need not be described herein in detail. Examples of pharmaceutically acceptable salts of the peptides and derivatives thereof according to the invention, include base salts, e.g., derived from an appropriate base, such as alkali metal (e.g., lithium, sodium, potassium), alkaline earth metal (e.g., calcium, barium), magnesium, ammonium, and $NW_nH_m$ bases and salts wherein each of n and m are 0 to 4 and n+m is 4, and wherein W is a $(C_1-C_{18})$alkyl. Pharmaceutically acceptable salts of an acid group or an amino group include, but are not limited to, salts of organic carboxylic acids such as acetic, lactic, tartaric, malic, isothionic, lactobionic and succinic acids; organic sulfonic acids such as methanesulfonic, ethanesulfonic, benzenesulfonic and p-tolylsulfonic acids, and inorganic acids such as hydrochloric, sulfuric, phosphoric and sulfamic acids. Pharmaceutically-acceptable salts of a compound with a hydroxy group include, but are not limited to, the anion of the compound in combination with a suitable cation such as $Na^+$, and $NW_nH_m$, wherein W is a $(C_1-C_{18})$alkyl group, and n and m are 0 to 4, and n+m is 4.

A still further part of this invention is a pharmaceutical composition of matter for binding to bacterial endotoxins and thus useful for treating sepsis that comprises at least one of the binding peptides described above, mixtures thereof, and/or pharmaceutical salts thereof, and a pharmaceutically-acceptable carrier therefor. Such compositions are prepared in accordance with accepted pharmaceutical procedures, for example, as described in *Remington's Pharmaceutical Sciences*, seventeenth edition, ed. Alfonso R. Gennaro, Mack Publishing Company, Easton, Pa. (1985). An endotoxin-binding peptide of the invention or its salt may be formulated together with the carrier into any desired unit dosage form. Typical unit dosage forms include tablets, pills, powders, solutions, suspensions, emulsions, granules, capsules, suppositories; injectable solutions and suspensions are particularly preferred.

Each carrier must be "acceptable" in the sense of being compatible with the other ingredients in the formulation and not injurious to the patient. The carrier must be biologically acceptable and inert, i.e., it must permit the cell to conduct its metabolic reactions so that the compound of this invention may effect its inhibitory activity.

Formulations include those suitable for oral, rectal, nasal, topical (including buccal and sublingual), vaginal and parenteral (including subcutaneous, intramuscular, intravenous, intradermal, and transdermal) administration, with intravenous formulations being preferred.

For example, to prepare formulations suitable for injection, solutions and suspensions are sterilized and are preferably isotonic to blood. In making injectable preparations, carriers which are commonly used in this field can also be used, for example, water, ethyl alcohol, propylene glycol, ethoxylated isostearyl alcohol, polyoxylated isostearyl alcohol, polyoxyethylene sorbitol and sorbitate esters. In these instances, adequate amounts of isotonicity adjusters such as sodium chloride, glucose or glycerin can be added to make the preparations isotonic. The aqueous sterile injection solutions may further contain anti-oxidants, buffers, bacteriostats, and like additions acceptable for parenteral formulations.

The formulations may conveniently be presented in unit dosage form and may be prepared by any method known in the art of pharmacy. Such methods include the step of bringing into association the active ingredient with the carrier which may encompass one or more accessory ingredients. In general, the formulations are prepared by uniformly and intimately bringing into association the active ingredient with liquid carriers or finely divided solid carriers or both, and then if necessary shaping the product. Various unit dose and multidose containers, e.g., sealed ampules and vials, may be used, as is well known in the art.

In addition to the ingredients particularly mentioned above, the formulations of this invention may also include other agents conventional in the art for this type of pharmaceutical formulation.

The endotoxin-binding peptides of the invention may be present in the composition in broad proportion to the carrier. For instance, the peptides may be present in the amount of 0.01 to 99.9 wt %, and more preferably in about 0.1 to 99 wt %. Still more preferably, the peptides may be present in an amount of about 1 to 70 wt % of the composition.

Therapeutic Methods

Also part of this invention is a method of removing bacterial endotoxin from the circulation of a patient, by administering to that patient an effective amount of one or more of the endotoxin-binding peptides of the present invention sufficient to remove bacterial endotoxin from the patient's blood circulatory system, pharmaceutically acceptable salts thereof, or mixtures thereof. The present invention further provides a method for treating or preventing sepsis comprising administering, to a patient in need of such treatment, one or more of the peptides described above. For therapeutic use in a method of inhibiting sepsis, activity, a peptide, or its salt, can be conveniently administered in the form of a pharmaceutical composition containing a peptide, or its salt, and a pharmaceutically acceptable carrier therefor. Suitable carriers are well known in the art and vary with the desired form and mode of administration of the pharmaceutical composition. For example, they may include diluents or excipients such as fillers, binders, wetting agents, disintegrators, surface-active agents, lubricants, and the like. Typically, the carrier may be a solid, liquid, or vaporizable carrier, or combinations thereof. In one preferred embodiment, the composition is a therapeutic composition and the carrier is a pharmaceutically acceptable carrier. In this application, "patient" will encompass any mammal that is suffering from sepsis.

The dosage of the endotoxin-binding peptides, pharmaceutically acceptable salts thereof, or mixtures thereof, in the compositions of the invention administered to a patient will vary depending on several factors, including, but not limited to, the age, weight, and species of the patient, the general health of the patient, the severity of the symptoms, whether the composition is being administered alone or in combination with other antiviral agents, the incidence of side effects and the like.

In general, a dose suitable for application to a patient in need of treatment for sepsis is about 0.001 to 100 mg/kg body weight/dose, preferably about 0.01 to 60 mg/kg body weight/dose, and still more preferably about 0.1 to 40 mg/kg body weight/dose. The desired dose may be administered as 1 to 6 or more subdoses administered at appropriate intervals as required. The compounds may be administered repeatedly, or it may be slowly and constantly infused to the patient. Higher and lower doses may also be administered.

The dose may be adjusted taking into account, for example, the above-identified variety of parameters. Typically, the present compositions may be administered in an amount of about 0.001 to 100 mg/kg body weight/day. However, other amounts may also be administered.

To achieve good plasma concentrations, the active compounds may be administered, for instance, by intravenous injection of an approximate 0.1 to 1% solution of the active ingredient, optionally in saline.

The active ingredient may be administered for therapy by any suitable route, including topical, oral, rectal, nasal, vaginal and parenteral (including intraperitoneal, subcutaneous, intramuscular, intravenous, intradermal, and transdermal) routes. It will be appreciated that the preferred route will vary with the condition and age of the patient, the nature of the disorder and the chosen active ingredient including other therapeutic agents. Preferred is the intravenous route. However, other routes may also be utilized depending on the conditions of the patient and how long-lasting the treatment is.

While it is possible for the active ingredient to be administered alone, it is preferably present as a pharmaceutical formulation. The formulations of the present invention comprise at least one active ingredient, as defined above, together with one or more acceptable carriers thereof and optionally other therapeutic agents.

The above method may be practiced by administration of the compounds by themselves or in a combination with other active ingredients, including antiviral compounds and/or antibiotic agents in a pharmaceutical composition. Other active agents suitable for use herein are any compatible drugs that are effective by the same or other mechanisms for the intended purpose, or drugs that are complementary to those of the present agents. These include agents that are effective antibiotic agents.

The compounds utilized in combination therapy may be administered simultaneously, in either separate or combined formulations, or at different times than the present compounds, e.g., sequentially, such that a combined effect is achieved. The amounts and regime of administration will be adjusted by the practitioner, by preferably initially lowering their standard doses and then titrating the results obtained. The therapeutic method of the invention may be used in conjunction with other therapies as determined by the practitioner.

Diagnostic Uses

Because of their endotoxin-binding properties, the peptides of the present invention may be used detect endotoxin in vitro in samples suspected of containing endotoxin. Such samples could include, for example, physiological fluids, including plasma, saliva, urine, or feces or in tissue samples. In addition, the specified helix family peptides can be used as a diagnostic tool to detect endotoxin in plasma fractionation products and virtually all other pharmaceutical preparations intended for human or veterinary use.

For use in such diagnostic tests, the peptides of the present invention may be labeled using any of a variety of labels and methods of labeling. Examples of types of labels which can be used in the present invention include, but are not limited to, enzyme labels, radioisotopic labels, non-radioactive isotopic labels, fluorescent labels, toxin labels, and chemiluminescent labels.

Examples of suitable enzyme labels include malate hydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, acetylcholine esterase, etc.

Examples of suitable radioisotopic labels include $^{3}$H, $^{125}$I, $^{131}$I, $^{32}$P, $^{35}$S, $^{14}$C, $^{51}$Cr, $^{57}$To, $^{58}$Co, $^{59}$Fe, $^{75}$Se, $^{152}$Eu, $^{90}$Y, $^{67}$Cu, $^{217}$Ci, $^{211}$At, $^{212}$Pb, $^{47}$Sc, and $^{109}$Pd.

Examples of suitable fluorescent labels include a $^{152}$Eu label, a fluorescein label, an isothiocyanate label, a rhodamine label, a phycoerythrin label, a phycocyanin label, and allophycocyanin label, an o-phthaldehyde label, an fluorescamine label, etc.

Examples of suitable toxin labels include diphtheria toxin, ricin, and cholera toxin. Examples of chemiluminescent labels include a luminal label, an isoluminal label, an aromatic acridinium ester label, and imidazole label, and acridinium salt label, an oxalate ester label, a luciferin label, a luciferase label, an aequorin label, etc.

Those of ordinary skill in the art will know of other suitable labels which may be employed in accordance with the present invention. The binding of these labels to the peptides of the present invention can be accomplished using standard techniques commonly known to those of ordinary skill in the art.

Detection of the peptides of the present invention with or without endotoxin bound may be accomplished with or without the use of such labels by a variety of means which are well known in the art including for example CD, UV/VIS spectroscopy, fluorescence spectroscopy, and NMR spectroscopy, etc. alone or in combination with means for separating and or identifying complex mixtures including for example affinity capillary electrophoresis, gel shift assay, affinity chromatography, ion exchange chromatography, etc. Those of ordinary skill in the art will know of other suitable means for detection which may be employed in accordance with the present invention.

The detection of the peptides of the present invention may be improved through the use of carriers. Well-known carriers include glass, polystyrene, polypropylene, polyethylene, dextran, nylon, amylases, natural and modified celluloses, polyacrylamides, agaroses and magnetite. The nature of the carrier can be either soluble to some extent or insoluble for the purposes of the present invention. Those skilled in the art will note many other suitable carriers for binding the peptides of the present invention, or will be able to ascertain the same by use of routine experimentation.

Purification

Because of their endotoxin-binding properties, the specified helix family peptides can be immobilized on surfaces to act as an affinity trap for endotoxin in ultrafiltration or dialysis-type treatments. In such treatment systems, the peptides of the present invention will typically be bound to a solid support, and the material to be purified will be passed over the endotoxin-support matrix. In addition, the peptides of the present invention can also be used to bind and remove endotoxin from plasma fractionation products and virtually all other pharmaceutical preparations intended for human or veterinary use. Affinity purification methods in which the peptides of the present invention may be employed are well known in the art. Varying the parameters of such methods in order to employ the peptides of the present invention are routine.

Having now generally described this invention, the same will be better understood by reference to certain specific examples, which are included herein for purposes of illustration only and are not intended to be limiting of the invention or any embodiment thereof, unless so specified.

EXAMPLE 1

Neutralization of Endotoxin in Plasma or in Buffer Solutions

The presence of endotoxin may routinely be measured using, for example, a kinetic chromogenic method. The assay involves a complete set of enzyme reactions which are described in detail in the following publications, each of which is hereby incorporated by reference.

ENDOSAFE
LIMULUS AMEBOCYTE LYSATE ENDOCHROME-K™ package insert.
(Endosafe. Charleston, S.C.)
Pearson III, F., *Pyrogens/Endotoxins, LAL Testing and Depyrogenation*, 1985.
Watson, S., Levin, J., and Novltsky, T., *Progress in Clinical and Biological Research*, Endotoxins and their detection with the Limulus Amebocyte Lysate Test, 93.

In the course of the endotoxin assay, a calibration curve is prepared which is a plot of logarithm of the time of the kinetic endpoint of a chromogenic reaction versus the logarithm of known concentrations of endotoxin.

Thus, if endotoxin is added to aqueous buffer solutions or to plasma the amount of endotoxin present can be assayed by reference to the calibration curve. Similarly, if plasma, plasma fractions, patient samples or any test solution contains an endogenous level of endotoxin, the level can also be determined by reference to the calibration curve.

Endotoxin was purposely added to plasma to a final concentration of 10 ng/mL and increasing concentrations of the compounds Arg Helix #2 (a monomeric cationic helix peptide), Bis Arg Helix #2 (which contains 2 copies of Arg Helix #2), Tris Arg Helix #3 (which contains 3 copies of Arg Helix #3), Tetra Arg Helix #3 (4 copies of Arg Helix #3) or Tris Arg Helix #3 (constrained) (3 copies of Arg Helix #3 constrained by design to present a "binding groove" within the molecule) were added to these same samples (Table 1).

TABLE 1

Percent Neutralization of Endotoxin Purposely Added to Plasma by Different Cationic Helix Family Peptides

| Cationic Helix Peptide | Peptide Concentration (mg/mL) | Percent binding of Endotoxin |
| --- | --- | --- |
| Arg Helix #2 | 0.01 | 0.00 |
| | 0.1 | 39.5 |
| | 0.5 | 51.2 |
| | 1.0 | 60.5 |
| Bis Arg Helix #2 | 0.01 | 0.00 |
| | 0.1 | 24.7 |
| | 0.5 | 51.2 |
| | 1.0 | 63.5 |
| Tris Arg Helix #3 | 0.01 | 24.7 |
| | 0.1 | 78.5 |
| | 0.5 | 73.7 |
| | 1.0 | 99.0 |
| Tetra Arg Helix #3 | 0.01 | 67.9 |
| | 0.1 | 67.9 |
| | 0.5 | 91.5 |
| | 1.0 | 99.0 |
| Tris Arg Helix #3 | 0.01 | 39.5 |
| | 0.1 | 95.0 |
| | 0.5 | 100 |
| | 1 | 100 |

As shown, in the presence of the higher helix copy peptides, endotoxin is completely neutralized in dose dependent fashion. Interestingly, the single copy peptide, Arg Helix #2, and Bis Arg Helix #2 (the peptide which contains only 2 copies of Arg Helix #2) possess very little neutralization (binding) activity. Similarly, other cationic proteins (such as protamine) were ineffective in neutralizing endotoxin. The ability of Tris Arg Helix #3 (constrained) to bind higher concentrations of endotoxin was also demonstrated (Table 2).

TABLE 2

Neutralization of Increasing Concentrations of Endotoxin by Tris Arg Helix #3 (Constrained)

| Endotoxin | Tris Arg Helix #3 | Percent Binding of |
| --- | --- | --- |
| 5 | 0.1 | 56.2 |
| | 1.0 | 100 |
| | 2.5 | 100 |
| 50 | 0.1 | 6.3 |
| | 1.0 | 99.8 |
| | 2.5 | 100 |
| 500 | 0.1 | 0 |
| | 1.0 | 97.7 |
| | 2.5 | 100.0 |

Even at concentrations of endotoxin as high as 500 ng/mL, as little as 1 mg/mL Tris Arg Helix #3 (constrained) caused nearly 100% neutralization of the endotoxin present in the sample. These same results were obtained with endotoxin added to aqueous samples and it made no difference whether the endotoxin and cationic helix peptide were added simultaneously to the plasma or whether endotoxin was added first followed by addition of the helix peptide. In either case, at the appropriate dose of helix peptide, all of the endotoxin was bound and removed from the test solution.

EXAMPLE 2

Effect of Binding Endotoxin on the Structure of Tris Arg Helix #3 (Constrained); Determination of the Dissociation Constant Circular dichroism (CD) spectroscopy can be used to determine the fractional percent of secondary structural elements present in a peptide preparation. Titration CD spectroscopy can be used to assess the effect of binding a ligand on the reorganization of peptide structure (You, Scarsdale, and Harris 1991; Sobel, Soler, et al 1992; Soler, Sobel and Harris 1992; Tyler-Cross, Sobel et al 1993; Tyler-Cross, Sobel, Marques et al, 1994). Thus, incremental amounts of endotoxin were added to a solution of TR3 CONST and the effect of binding endotoxin by the peptide was assessed by CD spectroscopy.

Figure 3:
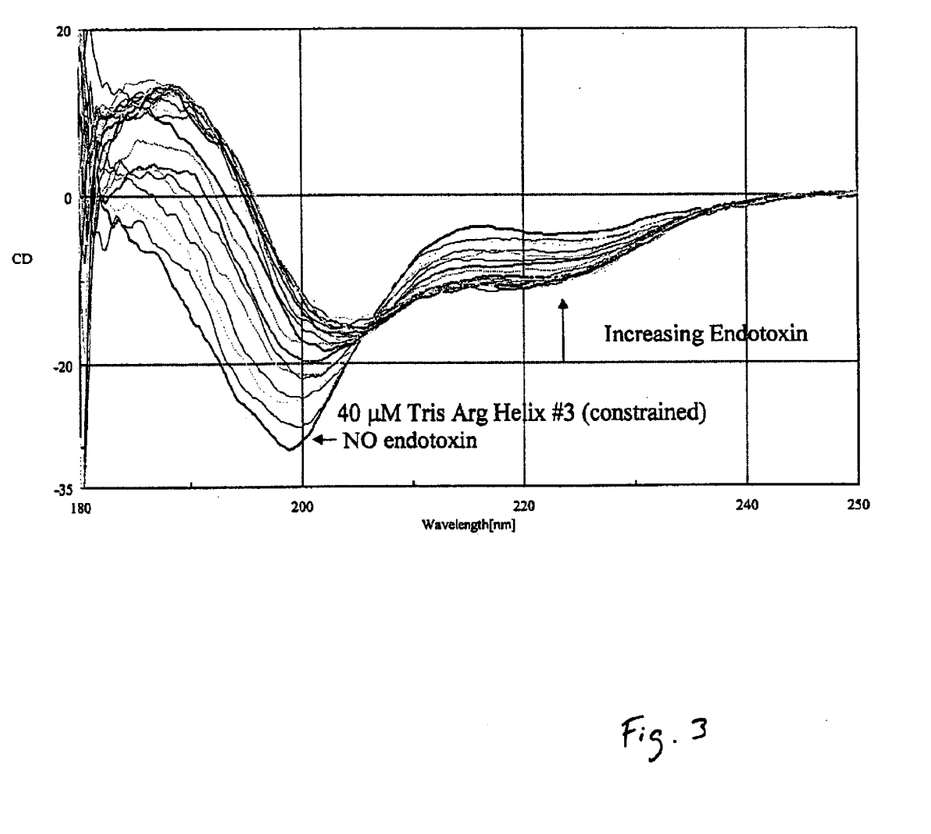
FIG. 3. Circular Dichroism Spectra of TR3 CONST as a Function of Endotoxin concentration.
Figure 4:
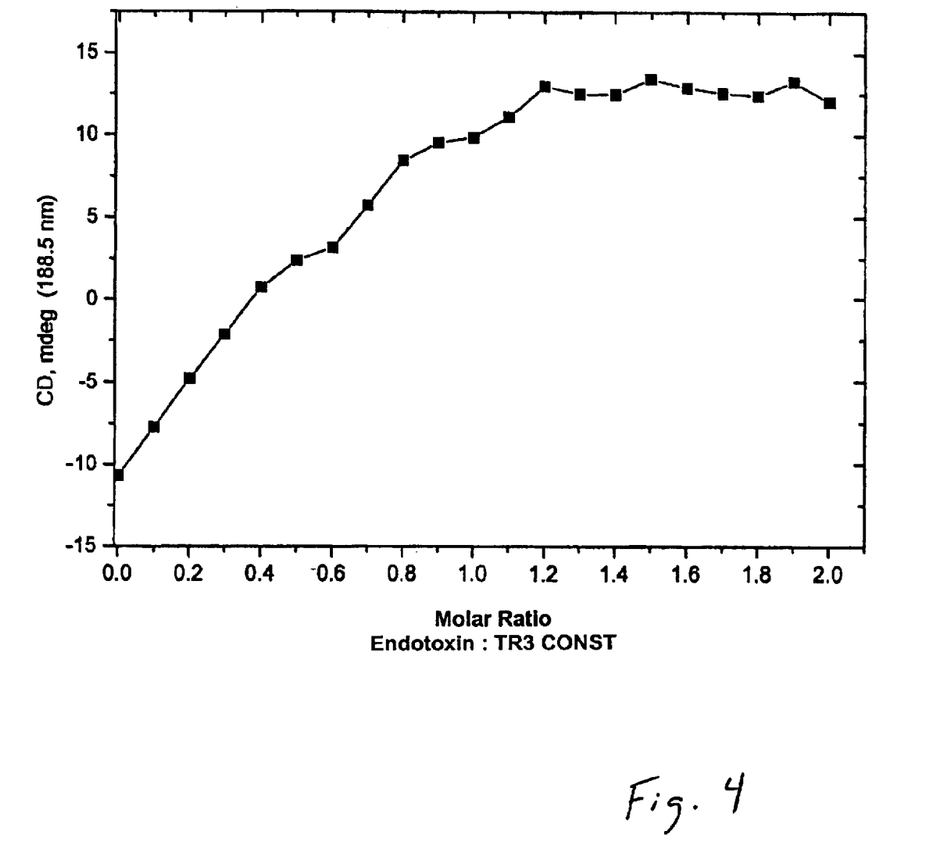
FIG. 4. Change in Circular Dichroism Ellipticity of TR 3 CONST as a function of the molar ratio of complexation.

By CD, Tris Arg Helix #3 (constrained) is 18% helix in solution (20° C.) but complexation with endotoxin increases the helix character of the peptide to nearly 50% (FIG. 3). Note that binding of endotoxin is dose dependent and saturable. If the increase in helix content (CD, mdeg) is re-plotted as a function of increasing endotoxin concentration (FIG. 4), it is possible to calculate the stoichiometry of binding (N) and the apparent equilibrium dissociation constant ($K_D$) according to the equation:

$$K_{D\ Apparent} = (K_D + N^* M_i)/2$$

where:
$K_D$ = dissociation constant
N = stoichiometry of binding (endotoxin:Tris Arg Helix#3 constrained)
$M_i$ = initial concentration of Tri Arg Helix #3 (constained)
Thus, the $K_D$ for binding endotoxin was found to be 0.87 μM and N=0.91; that is, approximately 1 mol endotoxin is bound per mol of TR3 CONST.

EXAMPLE 3

Tris Arg Helix #3 (Constrained) Binds Endotoxin as Presented by Intact *Escherichia Coli*; Assessment of Binding by Endotoxin Assay LPS is presented on the surface of gram-negative bacteria, such as *Escherichia coli* (*E. coli*). It was thus of interest to determine whether TR3 CONST would bind LPS present on whole bacterial cells. The assay method used was the endotoxin chromogenic assay as described above.

Thus, increasing amounts of *E. coli* (strain JM 109) were incubated (10 min; 37° C.) in the presence or absence of 200 µg/mL TR3 CONST in 10 mM phosphate-150 mM NaCl-3 mM KCl buffer, pH 7.4. An aliquot of the incubation mixture was then assayed for residual endotoxin activity as previously described.

As shown (Table 3), TR3 CONST (at 200 µg/mL) caused complete neutralization of the endotoxin activity presented by concentrations of *E. coli* up to 3e06 organisms/mL. At higher bacteria concentrations, there was lesser neutralization, but even at 3e08 per mL, TR3 CONST caused better than 90% neutralization of residual endotoxin activity. At higher bacteria concentrations, there was lesser neutralization, but even at 3e08 per mL, TR3 CONST caused better than 90% neutralization of residual endotoxin activity.

TABLE 3

Neutralization of Endotoxin Presented by Intact *E. coli* by a Fixed Concentration of TR3 CONST[a]

| E. coli (organisms/mL) | TR3 CONST (µg/mL) | Endotoxin Equivalents (ng/mL) | % neutralization |
|---|---|---|---|
| 3e03 | 0.00 | 1.0 | — |
|  | 200 | 0.00 | 100 |
| 3e04 | 0.00 | 4.1 | — |
|  | 200 | 0.00 | 100 |
| 3e05 | 0.00 | 24.7 | — |
|  | 200 | 0.00 | 100 |
| 3e06 | 0.00 | 58.1 | — |
|  | 200 | 6.97 | 87.9 |
| 3e07 | 0.00 | 193.3 | — |
|  | 200 | 94.3 | 48.8 |
| 3e08 | 0.00 | 700.6 | — |
|  | 200 | 440.0 | 37.1 |

[a]The concentration of *E. coli* (strain JM 109) was determined spectrophotometrically.

Equivalent endotoxin concentrations are deduced by reference to the endotoxin calibration curve.

Figure 5:
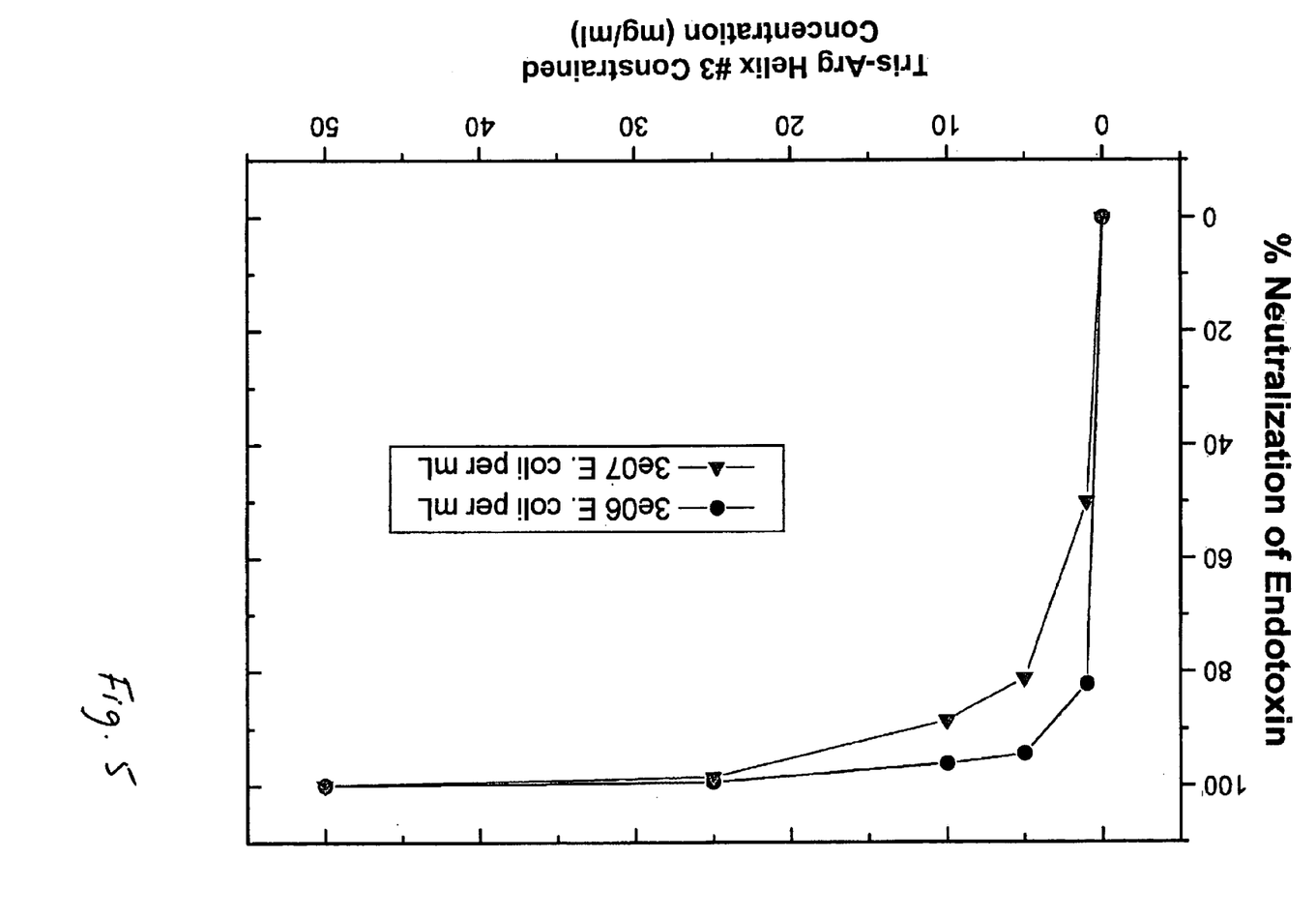
FIG. 5. Neutralization of Endotoxin as presented by Intact E. coli by Increasing Concentrations of TR 3 CONST.

Next, the concentration of *E. coli* was held constant in the presence of increasing concentrations of TR 3 CONST. As shown (FIG. 5), within 10 min incubation at 37° C., there is a dose dependent neutralization of endotoxin as presented on the surface of either 3e06 or 3e07 *E. coli* per mL.

Conclusions

The cationic helix peptides of the present invention, and in particular, the cationic helix peptides which contain at least three copies of the monomeric cationic helix sequence, are effective in binding and neutralizing endotoxin in plasma or aqueous samples. The cationic helix peptides have already proved safe as infused drugs in animal studies (Harris and Sobel 1999; Shenoy, Sobel et al. 1999; Harris and Sobel 2000) and in cell culture studies. Whether administered in a bolus IV or in a continuous infusion, the cationic helix peptides display no adverse cardiodynamic effects on mean arterial blood pressure, cardiac output, or pulmonary artery tension and show no adverse effects on blood borne cells, including red blood cells, white blood cells or platelets. It is thus very likely that the cationic helix peptides can be administered safely in high doses (as a prophylactic measure or in response to patient symptom on presentation to facilitate removal of endotoxin from the circulation) thus providing the physician with time necessary to address the systemic cause of infection.

Literature Cited

The following publications are representative of the state of the art and are incorporated herein by reference.

Dellinger, R- P., S. M. Opal, et al. (1997). "From the Bench to the Bedside: the Future of Sepsis Research." *Chest III*: 744–753.

Ferguson, A. D., W. Welte, et al. (2000). "A conserved structural motif for lipopolysaccharide recognition by procaryotic and eucaryotic proteins." *Struct Fold Des* 15: 585–592.

Harris, R- B. and M. Sobel (I 999). Heparin Binding Peptides. U.S. Patent Office. USA, Commonwealth Biotechnologies, Inc. U.S. Pat. No. 5,877,153.

Harris, R. B. and M. Sobel (2000). Heparin Binding Peptides. US Patent Office. USA, Commonwealth Biotechnologies, Inc. CIP to U.S. Pat. No. 5,877,153.

Heinzelmann, M., M. A. Mercer-Jones, et al. (2000). "Heparin binding protein increases survival in murine fecal peritonitis." *Crit Care Med* 28: 2926–2931.

Hoffmann, J. N., W. H. Hartl, et al. (1996). "Effect of hemofiltration on hemodynamics and systemic concentrations of anaphyltoxins and cytokines in human sepsis." *Intensive Care Med* 22: 1360–1367.

Murphy, E. D., J. F. Fessler, et al. (1997). "Effects of continuous venovenous hemofiltration on cardiopulmonary function in a porcine model of endotoxin induced shock." *Am J. Vet Res* 58: 408–413.

Parrillo, J. E. (1993). "Pathogenic mechanisms in septic shock." *New Eng J Med* 328: 1471–1480.

Shenoy, S., M. Sobel, et al. (1999). "Development of Heparin Antagonists with Focused Biological Activity." *Curr Pharm Design* 5: 965–986.

Sobel, M., Soler, D. F., Kermode, J. C., and Harris, R. B. Identification, characterization, and synthesis of a heparin binding domain peptide of human von Willebrand factor. *J. Biol. Chem.* 267: 8857–8862, 1992.

Soler, D. F., Sobel, M., and Harris, R. B. Design and synthesis of a helix heparin binding peptide. *Biochemistry* 31: 5010–5016, 1992.

Tracey, K. J. (1994). Tumor necrosis factor-alpha. The Cytokine Handbook. A. Thomson. London, Academic Press: 289–304.

Tracey, K. J. and A. Cerami (1993). Tumor necrosis factor (cachectin) in septic endotoxic shock. Handbook of Mediator of Septic Shock. E. A. Neugebauer and J. W. Holoday. Boca Raton, CRC Press: 289–304.

Tyler-Cross, R., Sobel, M., Soler, D. F., and Harris, R. B. Heparin-von Willebrand Factor Binding as Assessed by Isothermal Titration Calorimetry and by Affinity Fractionation of Heparins Using Synthetic Peptides. *Arch. Biochem. Biophys.* 306: 528–533, 1993.

Tyler-Cross, R., Sobel, M., Marques, D., and Harris, R. B. Heparin Binding Domain Peptides of Antithrombin III: Analysis by CD Spectrometry and Isothermal Ligand Titration Calorimetry. *Protein Science* 3: 620–627, 1994.

You, J. L., Scarsdale, J. N., and Harris, R. B. Calorimetric and spectroscopic examination of the solution phase structures of prekallikrein binding domain peptides of high molecular weight kininogen. *J. Prot. Chem.* 10:301–312, 1991.

While the invention has been described and illustrated herein by references to various specific materials, procedures, and examples, it is understood that the invention is not restricted to the particular material, combinations of material, and procedures selected for that purpose. Numerous variations of such details can be implied and will be appreciated by those skilled in the art.

---

What is claimed is:

1. A method for treating sepsis comprising administering to a patent in need of such treatment a molecule selected from the group consisting of Arg Helix #2, Bis Arg Helix #2, Tris-Arg Helix #3, Tetra-Arg Helix #3, and Tris-Am Helix #3-Constrained.

2. A method according to claim 1, wherein the molecule is administered to the patient in a pharmaceutical composition comprising the molecule, and a pharmaceutically acceptable carrier therefor.

3. A method according to claim 1, wherein said molecule Is administered In conjunction with one or more antibiotics.

4. A method for detecting endotoxin in a sample comprising providing a molecule selected from the group consisting of Arg Helix #2, Bis Arg Helix #2, Tris-Arg Helix #3, and Tris-Arg Helix #3 Constrained, wherein the molecule is labeled with a detectable label;

contacting the sample with the labeled molecule, under conditions that permit the binding of the molecule to any endotoxin in the sample; and detecting the presence of any labeled molecule bound to endotoxin.

5. A method according to claim 4, wherein the label is a fluorescent label.

6. A method for removing endotoxin in a sample comprising providing a molecule selected from the group consisting of Arg Helix #2, Bis Arg Helix #2, Tris-Arg Helix #3, Tetra-Arg Helix #3, and Tris-Arg Helix #3 Constrained, wherein the molecule is bound to a solid support;

expecting the sample to the molecule bound to a solid support, under conditions that permit the binding of the molecule to any endotoxin in the sample; and collecting the sample.

7. A method for reducing endotoxin levels in the body of a patient, comprising administering to the patient a molecule selected from the group consisting of Arg Helix #2, Bis Arg Helix #2, Tris-Arg Helix #3, Tetra-Arg Helix #3, and Tris-Arg Helix #3 Constrained in an amount sufficient to bind endotoxin in the patient's body.

8. A method according to claim 7, wherein the molecule is administered to the patient in a pharmaceutical composition comprising the molecule, and a pharmaceutically acceptable carrier therefore.

9. A method according to claim 7, wherein the molecule is administered in conjunction with one or more antibiotics.

* * * * *